United States Patent
Akui

(10) Patent No.: US 12,422,664 B2
(45) Date of Patent: Sep. 23, 2025

(54) ENDOSCOPE AND MANUFACTURING METHOD FOR ENDOSCOPE

(71) Applicant: OLYMPUS CORPORATION, Tokyo (JP)

(72) Inventor: Nobuaki Akui, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 602 days.

(21) Appl. No.: 17/716,135

(22) Filed: Apr. 8, 2022

(65) Prior Publication Data
US 2022/0225858 A1 Jul. 21, 2022

Related U.S. Application Data

(63) Continuation of application No. PCT/JP2019/040318, filed on Oct. 11, 2019.

(51) Int. Cl.
*A61B 1/00* (2006.01)
*A61B 1/005* (2006.01)
*G02B 23/24* (2006.01)

(52) U.S. Cl.
CPC ........ *G02B 23/2476* (2013.01); *A61B 1/0011* (2013.01); *A61B 1/0014* (2013.01); *A61B 1/005* (2013.01)

(58) Field of Classification Search
CPC . Y10S 600/92; G02B 23/2476; A61B 1/0011; A61B 1/0014; A61B 1/005
See application file for complete search history.

(56) References Cited

U.S. PATENT DOCUMENTS

| | | | |
|---|---|---|---|
| 2002/0028982 A1 | 3/2002 | Takahashi | |
| 2009/0171158 A1* | 7/2009 | Matsuo | G02B 23/2476 600/139 |
| 2012/0271108 A1* | 10/2012 | Hoshino | A61B 1/00091 600/139 |
| 2013/0150667 A1* | 6/2013 | Mitamura | A61B 1/00064 600/104 |

(Continued)

FOREIGN PATENT DOCUMENTS

| | | |
|---|---|---|
| EP | 2 505 116 A1 | 10/2012 |
| JP | H06285020 A | 10/1994 |

(Continued)

OTHER PUBLICATIONS

International Search Report dated Dec. 10, 2019 received in PCT/JP2019/040318.
English abstract only of US 2015/230692 A1.

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

An endoscope of the present invention includes an endoscope insertion section in which a resin layer is formed in an outer circumference of a net-like pipe made of metal formed along a longitudinal axis and a conductive member, a part of one side edge portion of which pierces through the resin layer and comes into contact with the net-like pipe to conduct electricity, in which at the one side edge portion of the conductive member, a pointed portion that cuts a part of the resin layer and comes into contact with the net-like pipe is formed.

15 Claims, 8 Drawing Sheets

(56) References Cited

U.S. PATENT DOCUMENTS

| | | | | |
|---|---|---|---|---|
| 2014/0296636 A1* | 10/2014 | Hatano | ............... | A61B 1/00124 600/138 |
| 2015/0230692 A1* | 8/2015 | Matsuda | ............ | A61B 1/00096 600/110 |
| 2017/0265715 A1* | 9/2017 | Nishina | .................. | A61B 1/009 |
| 2020/0355907 A1* | 11/2020 | Wieters | .............. | G02B 23/2476 |

FOREIGN PATENT DOCUMENTS

| | | | |
|---|---|---|---|
| JP | 2002-078677 A1 | | 3/2002 |
| JP | 2004-329857 A | | 11/2004 |
| JP | 2011-067384 A | | 4/2011 |
| JP | 2013198566 A | * | 10/2013 |
| JP | 5698877 B1 | | 4/2015 |
| WO | 2011/089777 A1 | | 7/2011 |
| WO | 2014/168000 A1 | | 10/2014 |

* cited by examiner

ENDOSCOPE AND MANUFACTURING METHOD FOR ENDOSCOPE

CROSS REFERENCE TO RELATED APPLICATION

This application is a continuation application of PCT/JP2019/040318 filed on Oct. 11, 2019, the entire contents of which are incorporated herein by this reference.

BACKGROUND OF THE INVENTION

1. Field of the Invention

The present invention relates to an endoscope and, more particularly, to a structure of an end portion of an endoscope insertion section and a manufacturing method for the endoscope.

2. Description of the Related Art

In recent years, in a medical field, an industrial field, and the like, an endoscope configured to enable an operator to, by inserting an insertion section having an elongated tube shape into a body cavity or the like of a subject, observe a desired test target site in the body cavity or the like has been widely used.

An endoscope insertion section in the endoscope of this type generally includes a bending section that is capable of actively bending with bending operation performed on an operation member of an operation section and a flexible tube that receives an external force to passively bend.

As a conventional endoscope insertion section, for example, an endoscope insertion section of a so-called torque tube form formed by a three-layer structure including a tubular inner layer resin tube, a metal net wire (a braid) having a tube shape covering an outer surface of the inner layer resin tube, and an outer layer resin tube covering an outer surface of the metal net wire has been widely adopted. If such an endoscope insertion section of the three-layer structure is adopted, it is possible to realize a configuration having satisfactory transmissivity of rotation torque while maintaining a desired small diameter of the endoscope insertion section.

In the endoscope insertion section of the conventional type having such a configuration, as contrivance for realizing a thinner configuration while keeping initial performance, a member less easily bonded by an adhesive in nature (for example, a thermosetting member) is sometimes adopted as the outer layer resin tube.

On the other hand, in the conventional endoscope insertion section, for measures against static electricity and measures against unnecessary radiation of electromagnetic waves, for example, an endoscope insertion section adopting a configuration for dropping the metal net wire to a ground of an endoscope system including an endoscope to secure electromagnetic compatibility (EMC) has been widely adopted.

For example, an endoscope disclose by International Publication No. 2014/168000 includes a treatment instrument channel, a center of which is disposed in any one quadrant of an orthogonal coordinate system having a center of an insertion section as an origin, and a plurality of small signal cables, a center of each of which is disposed, in a bending section, in a quadrant different from the quadrant in which the treatment instrument channel is disposed of quadrants divided by one axis Y of the orthogonal coordinate system extending in an up-down direction in which the bending section bends. With this configuration, the electromagnetic compatibility (EMC) is secured and a plurality of cables are efficiently disposed not to buckle in the bending section to reduce the insertion section in diameter.

For example, as disclosed by Japanese Patent Application Laid-Open Publication No. 2004-329857 and Japanese Patent Application Laid-Open Publication No. 2011-67384, in order to fix an end portion of an endoscope insertion section to a predetermined part on an inside of an operation section, work for peeling, for example, a part of an outer layer resin tube to expose a metal net wire and applying fixing by bonding, soldering, or the like is performed. Then, work for securing a ground by, for example, binding the metal net wire and screwing the metal net wire to a terminal or soldering another lead wire to the metal net wire is performed.

SUMMARY OF THE INVENTION

An endoscope according to an aspect of the present invention includes: an endoscope insertion section in which a resin layer is formed in an outer circumference of a net-like pipe made of metal formed along a longitudinal axis; and a conductive member, a part of one side edge portion of which pierces through the resin layer and comes into contact with the net-like pipe to conduct electricity, wherein at the one side edge portion of the conductive member, a pointed portion that cuts a part of the resin layer and comes into contact with the net-like pipe is formed.

A manufacturing method for an endoscope according to an aspect of the present invention includes: forming a resin layer in an outer circumference of a net-like pipe made of metal; cutting a part of the resin layer with a pointed portion formed in a part of a conductive member; and bringing the pointed portion into contact with the net-like pipe to conduct electricity.

DETAILED DESCRIPTION OF THE PREFERRED EMBODIMENTS

In general, in the conventional endoscopes disclosed by International Publication No. 2014/168000, Japanese Patent Application Laid-Open Publication No. 2004-329857, and Japanese Patent Application Laid-Open Publication No. 2011-67384 described above and the like, time and cost are required for work relating to a manufacturing process. Therefore, there is a strong demand for simplification and omission of these kinds of work.

According to embodiments of the present invention explained below, it is possible to provide an endoscope inexpensive and excellent in electric safety in which, when an endoscope insertion section is fixed to a predetermined position of an operation section, the endoscope insertion section can be easily fixed by only simple assembly work and conductivity between an endoscope system and a metal net wire can be secured in a simple configuration and a stable state.

The present invention is explained below with reference to illustrated embodiments.

The respective drawings used for the following explanation are schematically shown. In order to show respective components in degrees of sizes recognizable on the drawings, dimension relations, scales, and the like of respective members are sometimes differentiated for each of the components and shown. Therefore, the present invention is not limited to only illustrated forms concerning quantities of the respective components, shapes of the respective components, ratios of sizes of the respective components, relative positional relations among the respective components, and the like described in the respective drawings.

First, a schematic configuration about an endoscope of the present invention is briefly explained below with reference to FIG. 1 and FIG. 2.

Figure 1:
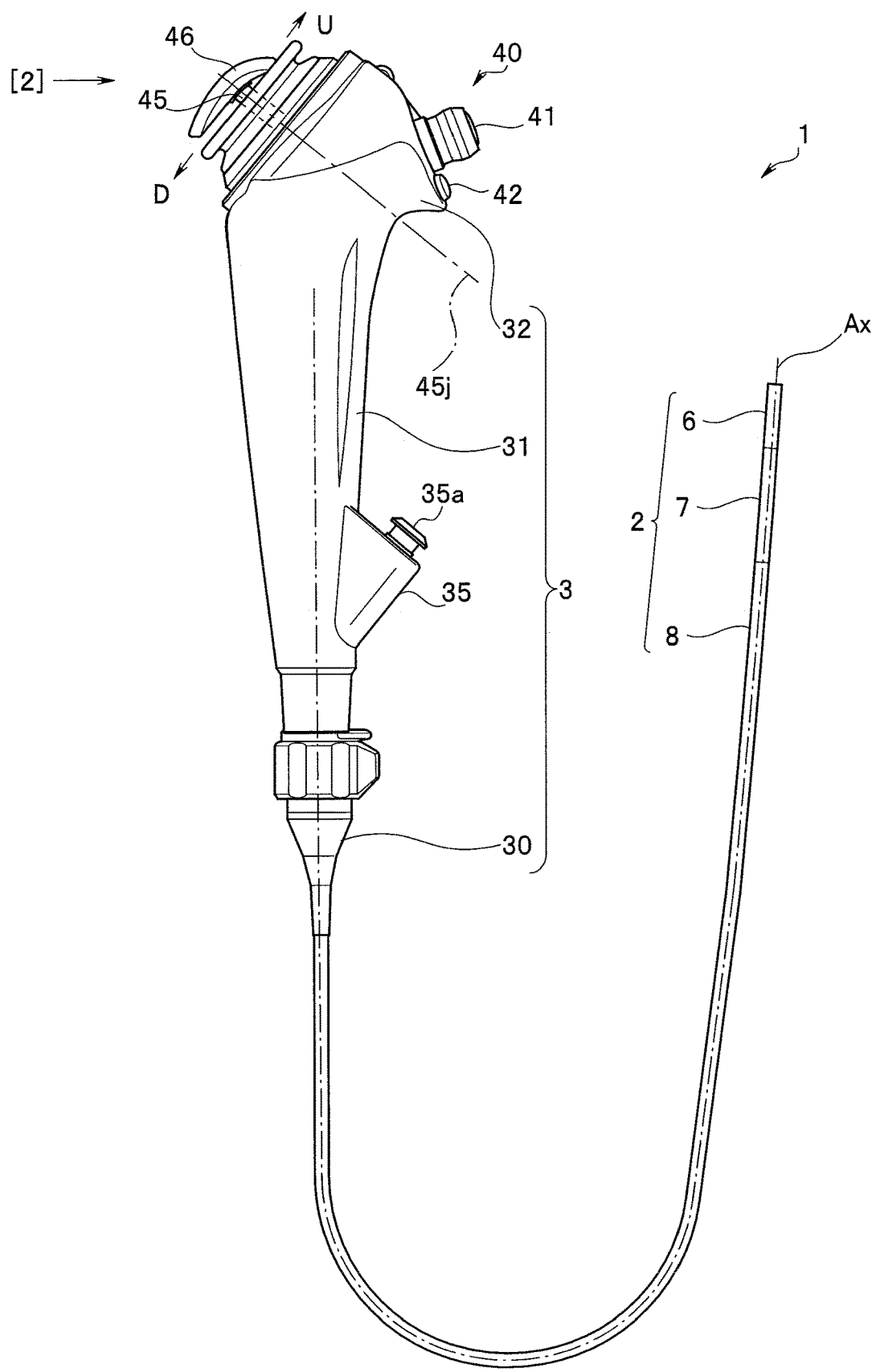
FIG. 1 is a plan view showing a schematic configuration of an endoscope of the present invention.

FIG. 1 is a plan view showing the schematic configuration of the endoscope of the present invention. FIG. 2 is a plan view showing an operation section of the endoscope shown in FIG. 1. FIG. 2 is a view in a direction indicated by an arrow sign [2] in FIG. 1.

As shown in FIG. 1, an endoscope 1 includes an endoscope insertion section (hereinafter simply abbreviated as insertion section) 2 formed in an elongated shape and an operation section 3 connected on a proximal end side of the insertion section 2. The endoscope 1 is, for example, an illustration of an endoscope for renal pelvis and urinary organs (nephroscope).

The insertion section 2 is configured by a tubular member having flexibility. The insertion section 2 is configured by consecutively connecting a distal end portion 6, a bending section 7, and a flexible tube section 8 in order from a distal end side along a longitudinal axis (hereinafter referred to as major axis) Ax.

Inside the distal end portion 6, although illustration is omitted, an image pickup unit for observing a test target site in a subject and picking up an image, an illumination unit that irradiates a region including the test target site with illumination light, and the like are disposed. Note that detailed explanation is omitted about a configuration of the distal end portion 6 assuming that the distal end portion 6 has the same configuration as a distal end portion of an insertion section of a conventional endoscope of the same type.

The bending section 7 is a bending mechanism that is formed by a plurality of bending pieces coupled along the major axis Ax and is actively bent by a predetermined bending mechanism (not shown). Note that detailed explanation is omitted about a configuration of the bending section 7 as well assuming that the bending section 7 has the same configuration as a bending section of the conventional endoscope of the same type.

The flexible tube section 8 is configured by a tubular member having flexibility capable of passively bending. Although illustration is omitted, a plurality of bending wires included in the bending mechanism, a signal cable extended from the image pickup unit of the distal end portion 6, a light guide that supplies illumination light to the illumination unit of the distal end portion 6, a treatment instrument insertion channel, and the like are inserted through an inside of the flexible tube section 8.

A main part of the operation section 3 is configured by a bending preventing portion 30, a grasping section 31, an operation section main body 32, and the like.

The bending preventing portion 30 is disposed to cover an outer surface of a connecting portion of a proximal end of the flexible tube section 8 of the insertion section 2 and a distal end of the operation section 3. Consequently, the bending preventing portion 30 prevents forced bending near a proximal end portion of the flexible tube section 8.

The grasping section 31 is a part grasped by, for example, fingers of a user. The grasping section 31 is connected to a proximal end of the bending preventing portion 30. The grasping section 31 is formed to have a shape for enabling the user to grasp and operate the grasping section 31 with either a left hand or a right hand.

A treatment instrument insertion section 35 is formed in a part close to a distal end of the grasping section 31. The treatment instrument insertion section 35 is formed to include a treatment instrument insertion port 35a communicating with a treatment instrument insertion channel (not shown). The treatment instrument insertion port 35a is an opening into which various kinds of treatment instruments are inserted. Consequently, the treatment instruments are inserted into and removed from the treatment instrument insertion channel through the treatment instrument insertion port 35a.

The operation section main body 32 is connected to a proximal end side of the grasping section 31. As shown in FIG. 2, a universal cord 4 is extended from a side surface of the operation section main body 32. An endoscope connector and the like (not shown) are provided at a distal end of the universal cord 4.

An operation button group 40 for performing various kinds of operation of the endoscope 1 is provided on one side surface side of the operation section main body 32. The operation button group 40 includes, for example, a suction button 41 and a button switch 42.

The suction button 41 is an operation member detachably attachable to a suction cylinder 43 (see FIG. 2) provided in the operation section main body 32. The button switch 42 is, for example, a plurality of operation members of a push button type. Any functions desired by the user among various functions concerning the endoscope 1 can be allocated to the plurality of operation members of the button switch 42.

An operation lever member 45 in a bending operation device (not shown; present inside the operation section 3) for performing active bending operation for the bending section 7 is provided on another side surface of the operation section main body 32. The operation lever member 45 is mainly configured by a finger rest section 46 and a lever 45. Although illustration is omitted, a proximal end of the lever 45 is axially supported to be tiltable in up-down and left-right directions with a spindle 45j as a rotation center axis with respect to an internal fixing section of the operation section 3. The finger rest section 46 is fixed to a distal end of the lever 45.

Figure 2:
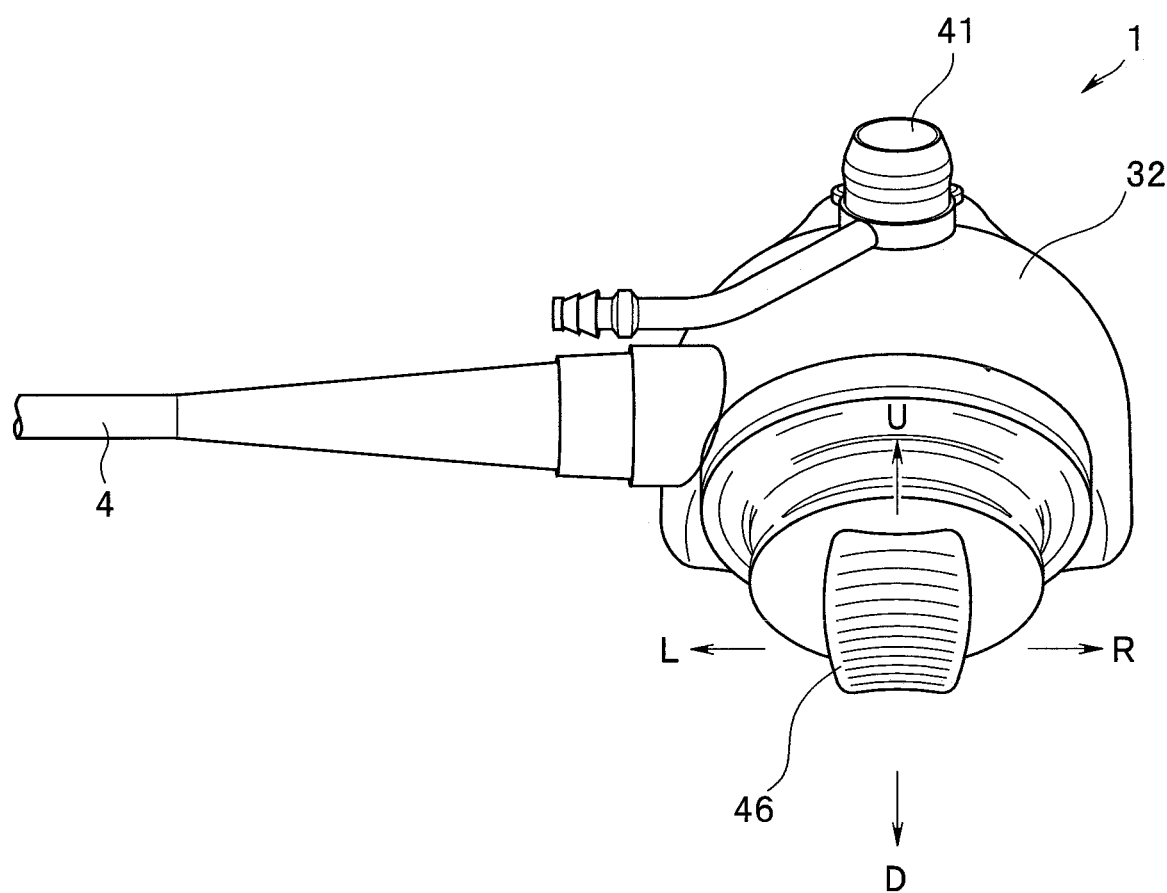
FIG. 2 is a plan view (a view in a direction indicated by an arrow sign [2] in FIG. 1) showing an operation section of the endoscope shown in FIG. 1.

The lever 45 is configured to be able to be tilted in directions indicated by arrow signs U, D, R, and L shown in FIG. 1 and FIG. 2 and intermediate directions of the directions by a finger of the user pressed against the finger rest section 46. Tilting operation of the lever 45 is operation associated with the bending operation of the bending section 7. Note that detailed explanation is omitted about the other components of the operation section 3 assuming that the other components are the same as the other components of the operation section of the conventional endoscope of the same type.

In the endoscope 1 configured as explained above, one end portion of the insertion section 2 is guided into the inside of the operation section 3 and fixed using predetermined means on the inside of the operation section 3.

First Embodiment

Structure of an end portion of an endoscope insertion section in a first embodiment of the present invention is explained below with reference to FIG. 3 to FIG. 5.

Note that the respective embodiments of the present invention relate to, in an endoscope insertion section, structure of an end portion on a side different from an end portion where a distal end portion is provided, the end portion being an end portion on a side guided into an inside of an operation section.

Figure 3:
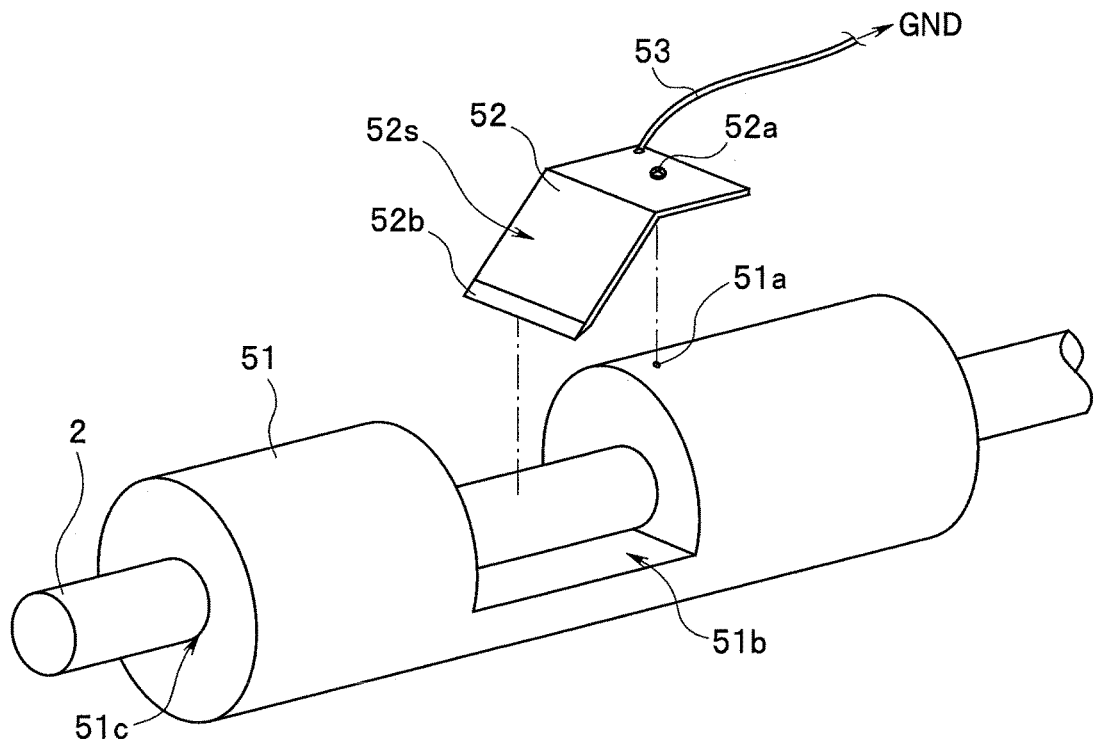
FIG. 3 is an exploded perspective view enlarging and showing an end portion of an endoscope insertion section in a first embodiment of the present invention.
Figure 4:
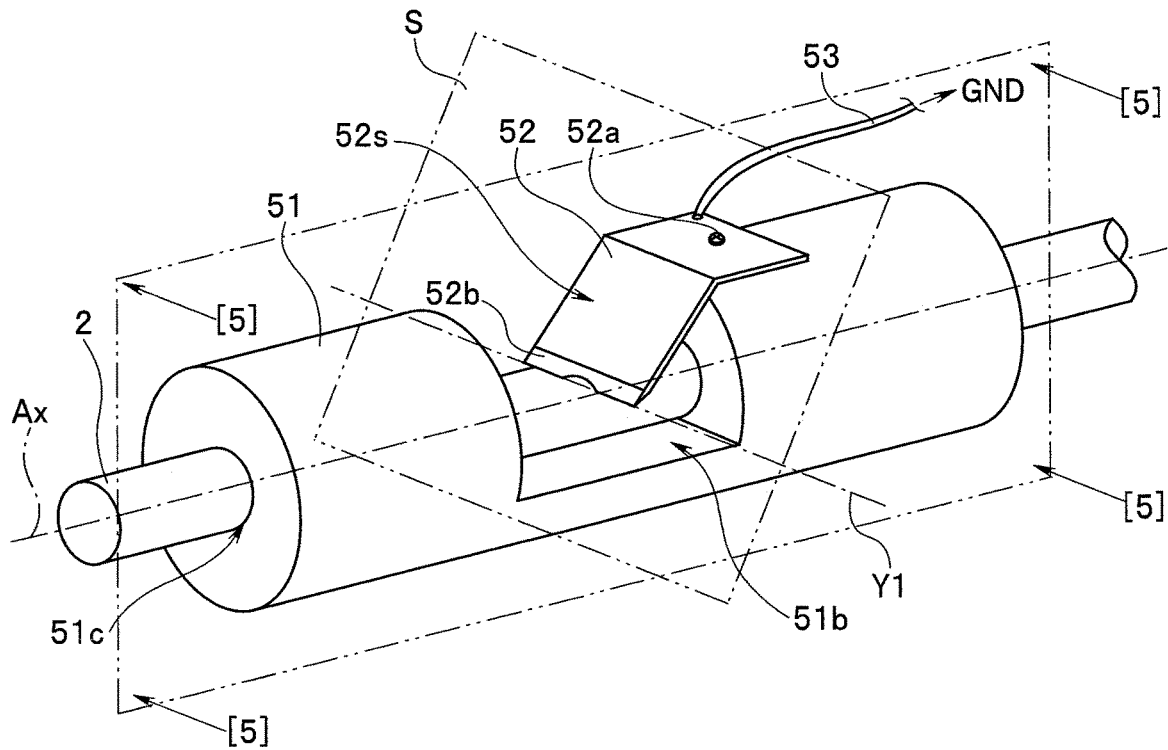
FIG. 4 is an assembly perspective view showing the end portion of the endoscope insertion section in the first embodiment of the present invention.
Figure 5:
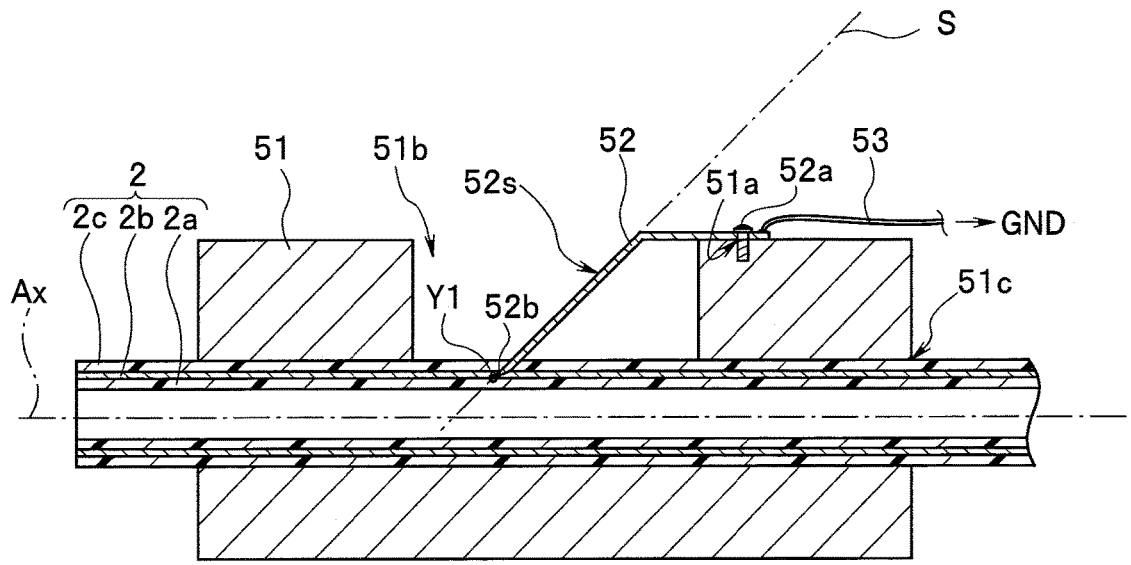
FIG. 5 is a sectional view taken along a cut section indicated by a sign [5] and indicated using an alternate long and two short dashes line in FIG. 4.

FIG. 3 to FIG. 5 are diagrams enlarging and showing the end portion of the endoscope insertion section in the first embodiment of the present invention. Among the figures, FIG. 3 is an exploded perspective view showing the end portion of the endoscope insertion section in the present embodiment. FIG. 4 is an assembly perspective view showing the end portion of the endoscope insertion section in the present embodiment. FIG. 5 is a sectional view taken along a cut section indicated by a sign [5] and indicated using an alternate long and two short dashes line in FIG. 4.

A pipe sleeve 51 into which a part of the insertion section 2 is inserted and a conductive member 52 are disposed at an end portion of the insertion section 2 of an endoscope in the present embodiment.

As shown in FIG. 5, the insertion section 2 is formed by a torque tube form of three-layer structure by a tubular inner layer resin tube 2a, a tubular net-like pipe 2b made of metal, and a tubular outer layer resin tube 2c and is formed in an elongated tube shape as a whole.

The inner layer resin tube 2a is a tubular member made of resin and having flexibility, through an inside of which an image pickup signal cable, a control cable, and the like are inserted.

The net-like pipe 2b made of metal covers an outer surface of the inner layer resin tube 2a and is formed in a tubular shape along the major axis Ax. The net-like pipe 2b is formed by braiding a thin wire material made of metal in a tubular shape and is provided between the outer surface of the inner layer resin tube 2a and an inner surface of the outer layer resin tube 2c.

The outer layer resin tube 2c is a tubular resin layer made of resin and having flexibility that covers an outer circumference of the net-like pipe 2b.

The pipe sleeve 51 is formed to include an insertion hole 51c through which a part of the insertion section 2 is inserted, a cutout 51b, and a screw hole 51a. Illustration of the pipe sleeve 51 itself is omitted. However, the pipe sleeve 51 is a connecting member fixed to a fixing portion (not shown) on the inside of the operation section 3 using predetermined fixing means (not shown: for example, screw fastening or bonding).

The cutout 51b is formed such that a part of a side surface of the insertion section 2 can be visually recognized in a state in which the insertion section 2 is inserted into the insertion hole 51c of the pipe sleeve 51.

The screw hole 51a corresponds to a screw 52a for fixing the conductive member 52 to the pipe sleeve 51 when the conductive member 52 is inserted into the cutout 51b and disposed in a predetermined position in the cutout 51b. Therefore, the screw hole 51a is formed in a predetermined position near the cutout 51b.

The conductive member 52 is a plate-like member having, for example, a shape and a size insertable into the cutout 51b and formed using, for example, a metal member. The conductive member 52 includes a proximal end portion having the screw hole 51a and a slope 52s formed to incline from the proximal end portion to a distal end side. Further, in the conductive member 52, a pointed portion 52b is formed at one side edge portion which is a part of a circumferential edge portion of the slope 52s. The pointed portion 52b is formed to cut a part of the outer layer resin tube 2c (a resin layer) to come into contact with the net-like pipe 2b when the conductive member 52 is inserted into the cutout 51b and disposed in the predetermined position in the cutout 51b. Therefore, the pointed portion 52b is formed thin and sharp and formed in a so-called edge shape to, for example, cut the outer layer resin tube 2c and reach the net-like pipe 2b.

An earth cable 53 functioning as an earth section electrically earthed to an endoscope system (not shown) including the endoscope 1 is connected and fixed to the conductive member 52 using soldering or the like. The earth cable 53 is extended from the operation section 3 to the endoscope system (not shown) through the universal cord 4.

With such a configuration, when the conductive member 52 is inserted into the cutout 51b and disposed in the predetermined position in the cutout 51b, electrical conductivity is secured between the net-like pipe 2b and the endoscope system (not shown) through the conductive member 52 and the earth cable 53.

When the conductive member 52 is inserted into the cutout 51b and disposed in the predetermined position in the cutout 51b, the conductive member 52 is fixed to the pipe sleeve 51 using the screw 52a, which is a fastening member. At this time, the conductive member 52 is in a state in which the pointed portion 52b cuts a part of the outer layer resin tube 2c and is in contact with the net-like pipe 2b. At this time, the conductive member 52 is in a state in which the pointed portion 52b cuts and bites into a part of the outer layer resin tube 2c to be fixed to the insertion section 2. In other words, the conductive member 52 is in a state in which a part of the pointed portion 52b pierces through the outer layer resin tube 2c and comes into contact with the net-like pipe 2b and is fixed to the insertion section 2.

Further, when the conductive member 52 is inserted into the cutout 51b and disposed in the predetermined position in the cutout 51b, as shown in FIG. 4 and FIG. 5, a surface S including the slope 52s as a part thereof is disposed to cross (that is, nonparallelly to) the major axis Ax. The pointed portion 52b is formed such that an axis Y1 extending along the pointed portion 52b and a plane orthogonal to the major axis Ax are parallel.

In other words, when the conductive member 52 is inserted into the cutout 51b and disposed in the predetermined position in the cutout 51b, the conductive member 52 is disposed in the cutout 51b such that the surface S including the slope 52s as a part thereof and the major axis Ax cross at a predetermined angle.

More specifically, for example, a case in which the conductive member 52 is disposed with respect to the insertion section 2 such that the surface S has an angle of approximately 45 degrees with respect to the major axis Ax is illustrated.

The other components of the endoscope 1 are substantially the same as components of a conventional endoscope generally put to practical use.

An end portion of the insertion section 2 in the present embodiment configured as explained above is assembled, for example, in a procedure explained below.

First, a part of the end portion of the insertion section 2 is inserted into the insertion hole 51c of the pipe sleeve 51. A part of the insertion section 2 is disposed in a predetermined part of the pipe sleeve 51.

Subsequently, the conductive member 52 is inserted into the cutout 51b of the pipe sleeve 51. At this time, the pointed portion 52b at one side edge portion of the conductive member 52 is disposed to cut a part of the outer layer resin tube 2c of the insertion section 2 and thereafter come into contact with the net-like pipe 2b of the insertion section 2. In this state, the conductive member 52 is fixed to the pipe sleeve 51 by, for example, the screw 52a.

The earth cable 53 is connected and fixed to the conductive member 52 using soldering or the like. Therefore, as explained above, the conductive member 52 and the net-like pipe 2b of the insertion section 2 are set in a contact state, whereby the net-like pipe 2b and the endoscope system (not shown) are in an electrically conductive state through the conductive member 52 and the earth cable 53.

As explained above, according to the first embodiment, the endoscope 1 includes the insertion section 2 in which the outer layer resin tube 2c (the resin layer) is formed in the outer circumference of the net-like pipe 2b made of metal formed along the major axis Ax, the pipe sleeve 51 into which a part of the insertion section 2 is inserted, the cutout 51b formed in the pipe sleeve 51, and the conductive member 52 inserted into the cutout 51b, the pointed portion 52b at one side edge portion of the conductive member 52 coming into contact with the net-like pipe 2b to conduct electricity.

With this configuration, in the present embodiment, it is possible to set, with a simple configuration, the conductive member 52 and the net-like pipe 2b of the insertion section 2 in the contact state. Consequently, it is possible to easily secure an electrically conductive state between the net-like pipe 2b and the endoscope system (not shown).

With the configuration in the present embodiment, compared with a conventional product, it is possible to simplify structure and contribute to simplification of a manufacturing process. Therefore, it is possible to contribute to a reduction in manufacturing cost as well.

Second Embodiment

Next, an endoscope in a second embodiment of the present invention is explained below with reference to FIG. 6 to FIG. 8.

Figure 6:
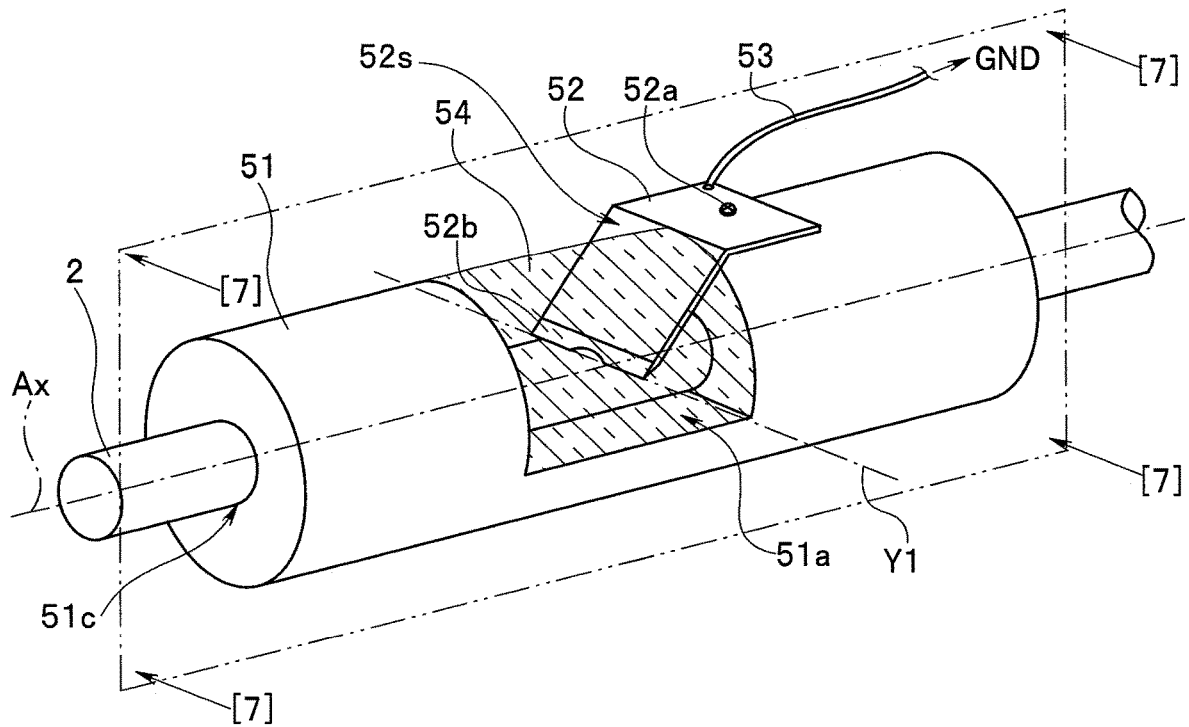
FIG. 6 is an assembly perspective view enlarging and showing an end portion of an endoscope insertion section in a second embodiment of the present invention.
Figure 7:
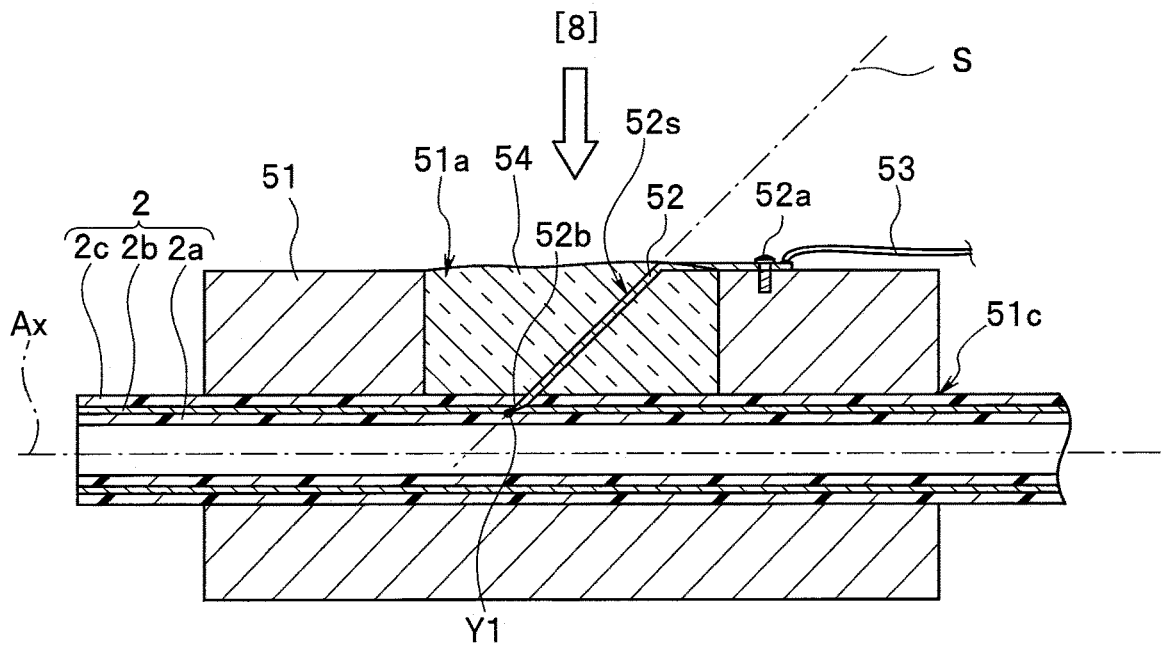
FIG. 7 is a sectional view taken along a cut section indicated by a sign [7] and indicated using an alternate long and two short dashes line in FIG. 6.
Figure 8:
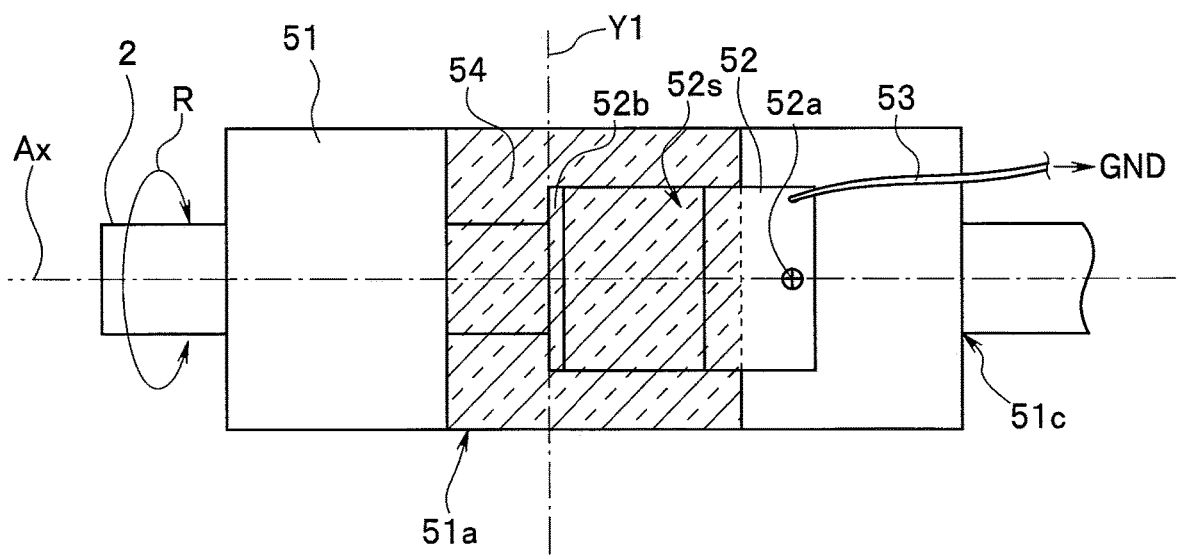
FIG. 8 is a plan view in an arrow sign [8] direction in FIG. 7.

FIG. 6 to FIG. 8 are diagrams enlarging and showing an end portion of an endoscope insertion section in the second embodiment of the present invention. Among the figure, FIG. 6 is an assembly perspective view showing the end portion of the endoscope insertion section in the present embodiment. FIG. 7 is a sectional view taken along a cut section indicated by a sign [7] and indicated using an alternate long and two short dashes line in FIG. 6. FIG. 8 is a plan view in an arrow sign [8] direction in FIG. 7.

A basic configuration in the present embodiment is substantially the same as the basic configuration in the first embodiment explained above. The present embodiment is only different in that the endoscope further includes an adhesive 54 as a fixing member for fixing the conductive member 52 to the insertion section 2. Therefore, the same components as the components in the first embodiment explained above are denoted by the same reference numerals and signs and explanation of the components is omitted.

In the present embodiment, the conductive member 52 is fixed to the insertion section 2 using the adhesive 54, which is the fixing member.

Therefore, the adhesive 54 is charged in the cutout 51b when the conductive member 52 is inserted into the cutout 51b of the pipe sleeve 51 and disposed in a predetermined position and the pointed portion 52b comes into contact with the net-like pipe 2b. At this time, in the cutout 51b, the adhesive 54 is charged to cover at least an outer surface of a portion where the pointed portion 52b is cut into the outer layer resin tube 2c of the insertion section 2.

Note that, as the adhesive 54, it is desirable to apply an adhesive in which thermosetting resin such as epoxy resin is used. In this case, depending on a material applied to the outer layer resin tube 2c, it is also likely that the adhesive 54 has a weak effect of bonding action to the outer layer resin tube 2c. However, even in this case, the adhesive 54 can function as the fixing member for fixing the conductive member 52 to the insertion section 2 by being charged in the cutout 51b of the pipe sleeve 51. The other components are completely the same as the other components in the first embodiment.

As explained above, according to the second embodiment, the endoscope further includes the fixing member (the adhesive 54) for fixing the conductive member 52 to the insertion section 2.

With the configuration in the present embodiment, the same effects as the effects in the first embodiment explained above can be obtained. At the same time, in the present embodiment, since the adhesive 54 is charged in the cutout 51b, a contact state of the conductive member 52 and the net-like pipe 2b of the insertion section 2 can be maintained in a more secure and stable state.

Further, when the insertion section 2 is inserted into the insertion hole 51c of the pipe sleeve 51, the conductive member 52 is inserted into the cutout 51b, and the pointed portion 52b of the conductive member 52 is disposed in a state in which the pointed portion 52b is cut into the outer layer resin tube 2c of the insertion section 2, for example, if an amount of force in a direction along the major axis Ax is applied to the insertion section 2, it is likely that a skin of the outer layer resin tube 2c is cut by the pointed portion 52b. However, in the configuration in the present embodiment, the adhesive 54 is charged in the cutout 51b. At this time, at least the adhesive 54 is charged to cover the outer surface of the portion where the pointed portion 52b is cut into the outer layer resin tube 2c of the insertion section 2. Therefore, when an amount of force in a predetermined direction is applied to the insertion section 2, the adhesive 54 prevents the outer layer resin tube 2c from being cut. Therefore, the adhesive 54 functions as the fixing member for fixing the conductive member 52 to the insertion section 2. Consequently, it is possible to surely secure a stable electrically conductive state between the net-like pipe 2b and the endoscope system (not shown).

Third Embodiment

In the first and second embodiments explained above, as a disposition form of the conductive member 52, only a form in which the axis Y1 extending along the pointed portion 52b is orthogonal to the major axis Ax is explained. However, the disposition form is not limited to this example.

A third embodiment of the present invention explained next is an illustration of a case in which a disposition form of a conductive member is different from the disposition form in the first and second embodiments explained above. A basic configuration in the present embodiment is substantially the same as the basic configurations in the first and second embodiments explained above. In the present embodiment, the disposition form of the conductive member, in particular, disposition of a pointed portion is only different. Therefore, the same components as the components in the first and second embodiments are denoted by the same reference numerals and signs and explanation of the components is omitted.

Figure 9:
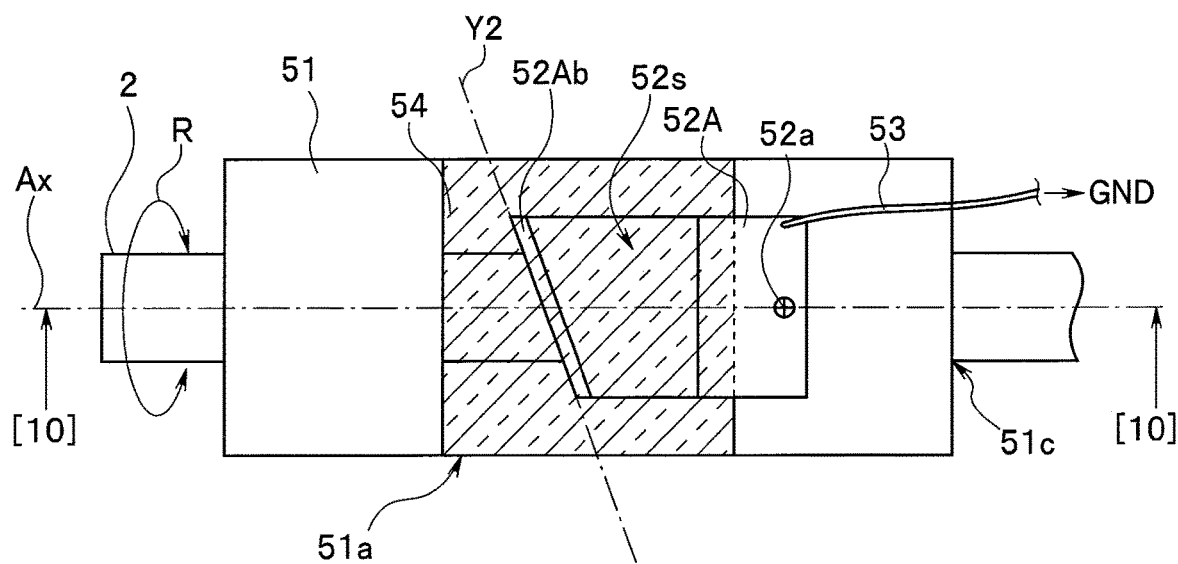
FIG. 9 is a plan view of an end portion of an endoscope insertion section in a third embodiment of the present invention viewed from an upper surface (a view in an arrow sign [9] direction in FIG. 10)
Figure 10:
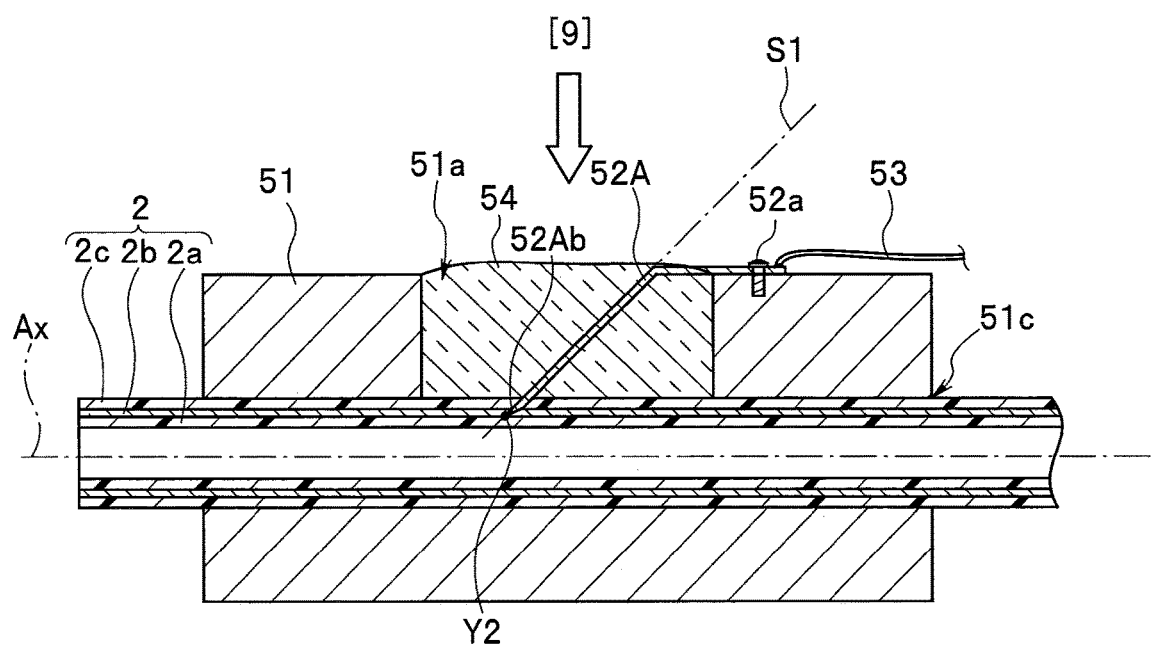
FIG. 10 is a longitudinal sectional view of the end portion of the endoscope insertion section in the third embodiment of the present invention.

FIG. 9 and FIG. 10 are diagrams enlarging and showing an end portion of an endoscope insertion section in the third embodiment of the present invention. Of the figures, FIG. 9 is a plan view of the end portion of the endoscope insertion section in the present embodiment viewed from an upper surface (a view in an arrow sign [9] direction in FIG. 10). FIG. 10 is a longitudinal sectional view of the end portion of the endoscope insertion section in the present embodiment (a view equivalent to FIG. 7 in the second embodiment).

As shown in FIG. 9, a pointed portion 52Ab of a conductive member 52A in the present embodiment is formed in a tilted form at a predetermined inclination angle with respect to a longitudinal direction of the conductive member 52A. In this case, when the conductive member 52A is disposed in a predetermined position in the cutout 51b, the pointed portion 52Ab is formed such that a plane orthogonal to the major axis Ax and an axis Y2 extending along the pointed portion 52Ab cross (that is, are non-parallel).

In this case as well, the conductive member 52A is disposed in the cutout 51b such that, as in the second embodiment explained above, a surface S1 including the slope 52s as a part thereof is nonparallel to the major axis Ax and the surface S1 and the major axis Ax cross at a predetermined angle. As in the second embodiment explained above, the adhesive 54 is charged in the cutout 51b. The other components are completely the same as the other components in the second embodiment explained above.

According to the third embodiment configured as explained above, the same effects as the effects in the second embodiment explained above can be obtained. At the same time, according to the present embodiment, the plane orthogonal to the major axis Ax and the axis Y2 extending along the pointed portion 52Ab are formed to cross (that is, nonparallel) when the conductive member 52A is disposed in the predetermined position in the cutout 51b. With this configuration, it is possible to easily and surely prevent movement in a rotating direction around the major axis Ax of the insertion section 2 (see a sign R in FIG. 9) in addition to movement in a direction along the major axis Ax of the insertion section 2 (movement in a forward and backward direction).

Therefore, with the configuration in the present embodiment, it is possible to more surely perform fixing of the conductive member 52A to the insertion section 2 and more surely secure electric stability.

Fourth Embodiment

Next, an end portion of an endoscope insertion section in a fourth embodiment of the present invention is explained below with reference to FIG. 11 to FIG. 14.

Figure 11:
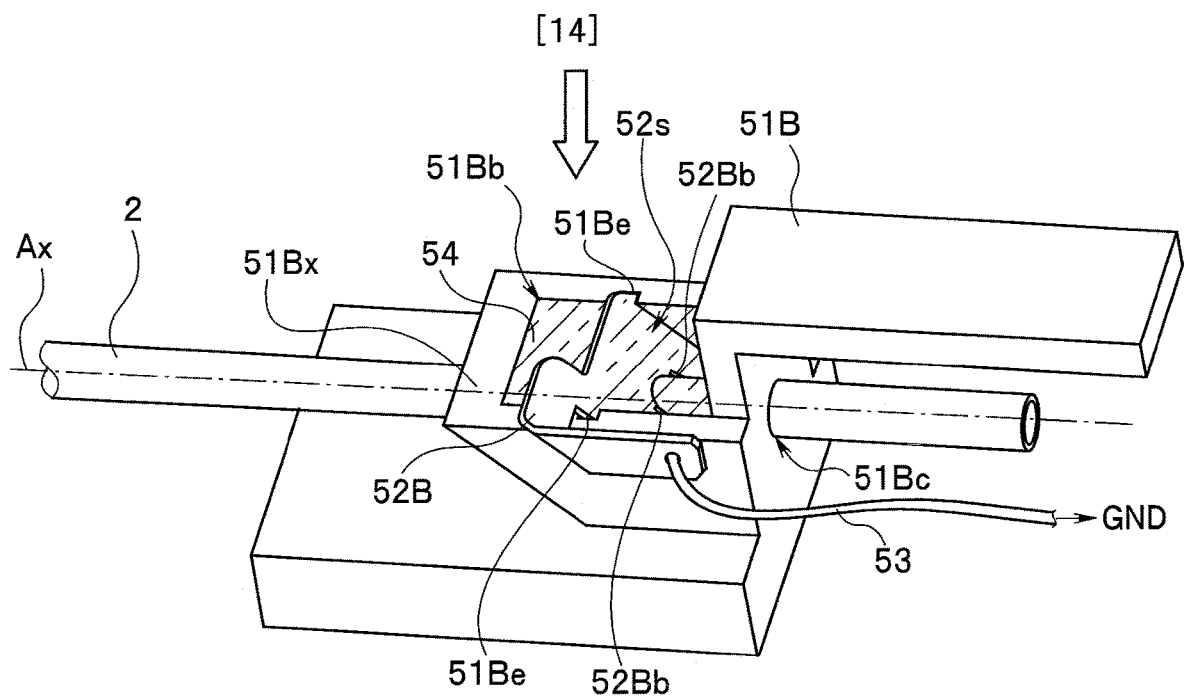
FIG. 11 is an assembly perspective view enlarging and showing an end portion of an endoscope insertion section in a fourth embodiment of the present invention.
Figure 12:
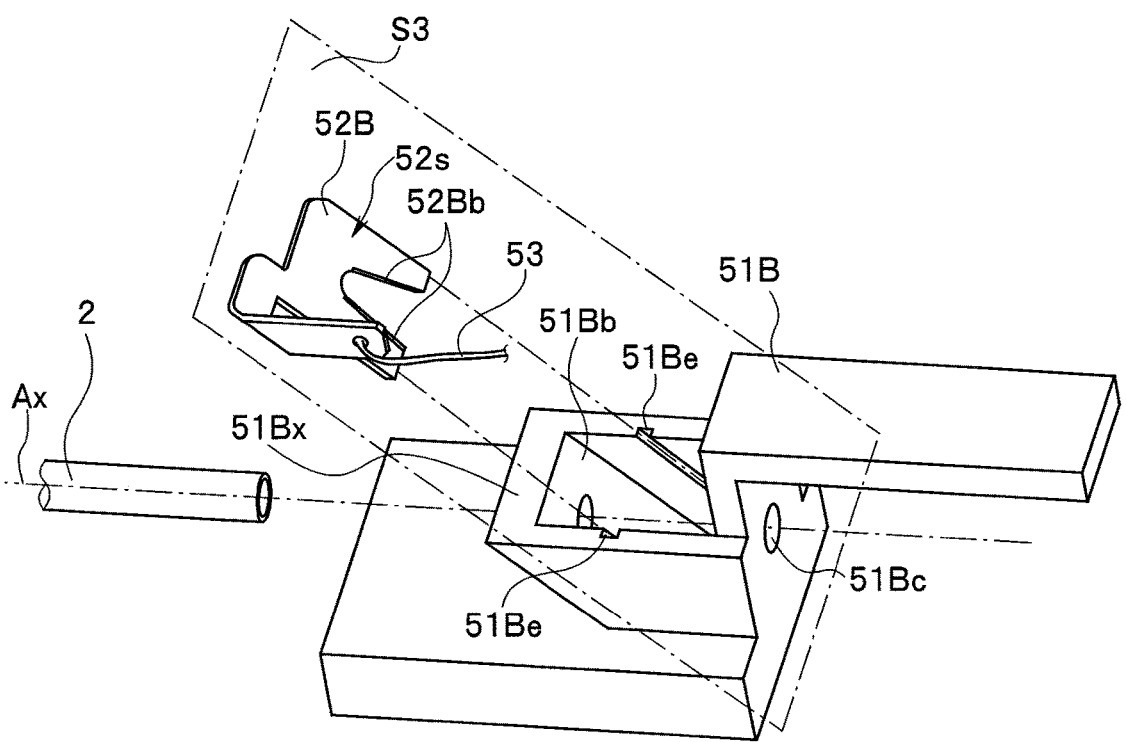
FIG. 12 is an exploded perspective view showing the end portion of the endoscope insertion section in the fourth embodiment of the present invention.
Figure 13:
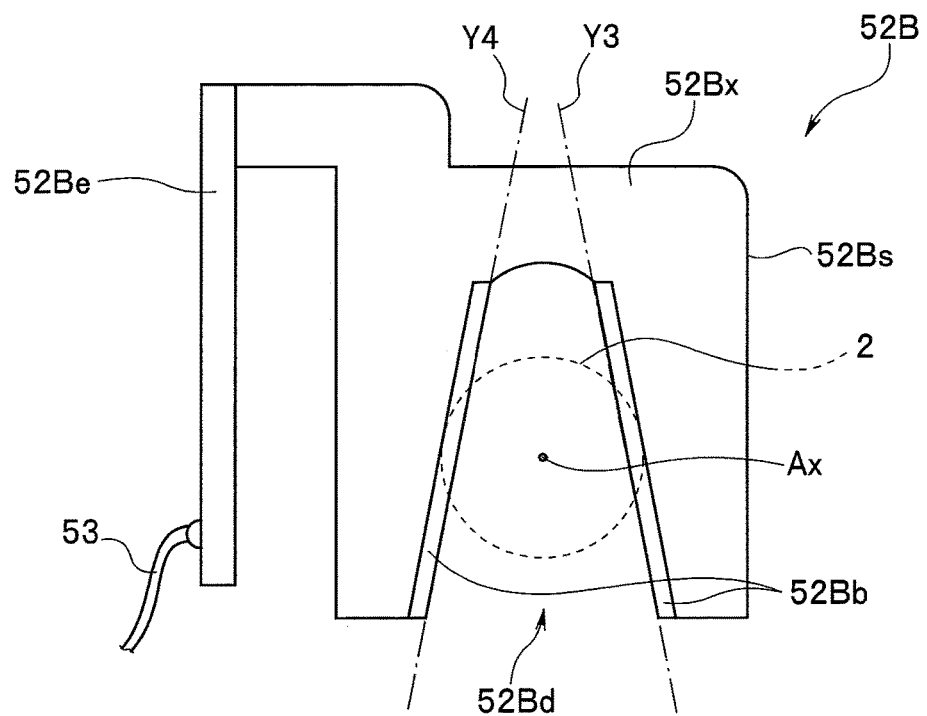
FIG. 13 is a plan view extracting, enlarging, and showing only a conductive member in the fourth embodiment of the present invention.
Figure 14:
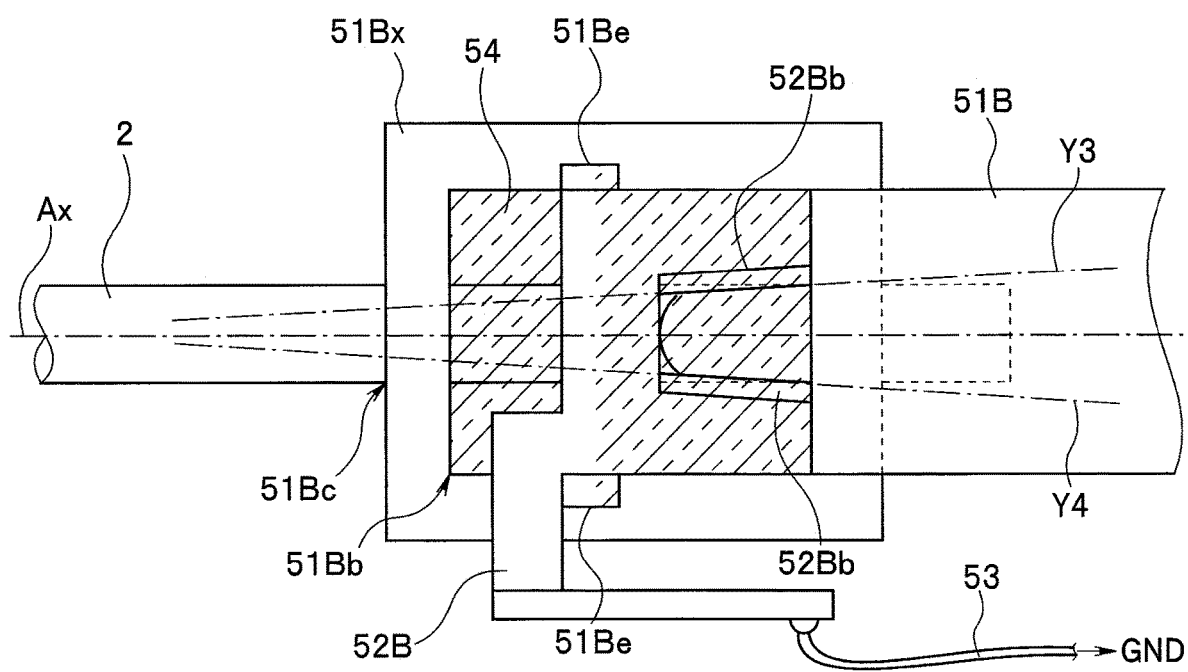
FIG. 14 is a plan view in an arrow sign [14] direction in FIG. 11.

FIG. 11 to FIG. 14 are diagrams enlarging and showing the end portion of the endoscope insertion section in the fourth embodiment of the present invention. Among the figures, FIG. 11 is an assembly perspective view showing the end portion of the endoscope insertion section in the present embodiment. FIG. 12 is an exploded perspective view showing the end portion of the endoscope insertion section in the present embodiment. FIG. 13 is a plan view extracting, enlarging, and showing only a conductive member in the present embodiment. FIG. 14 is a plan view in an arrow sign [14] direction in FIG. 11.

A basic configuration in the present embodiment is substantially the same as the basic configurations in the respective embodiments explained above. In the present embodiment, forms of a pipe sleeve 51B and a conductive member 52B are slightly different. Therefore, the same components as the components in the embodiments explained above are denoted by the same reference numerals and signs and explanation of the components is omitted. Only different portions are explained below.

As shown in FIG. 11 and the like, the pipe sleeve 51B in the present embodiment is formed to include a main body 51Bx having a bottomed box shape. The main body 51Bx includes an opening 51Bb on a surface facing a bottom surface. The opening 51Bb is formed such that a part of a side surface of the insertion section 2 can be visually recognized in a state in which the insertion section 2 is inserted into an insertion hole 51Bc of the pipe sleeve 51B. Therefore, the opening 51Bb of the pipe sleeve 51B in the present embodiment is a part equivalent to the cutout (51b) of the pipe sleeve (51) in the respective embodiments explained above.

In the main body 51Bx, the insertion hole 51Bc, through which the end portion of the insertion section 2 is inserted in the major axis Ax direction, is formed on each of two wall surfaces among four inner wall surfaces excluding the bottom surface. In this case, the insertion hole 51Bc is formed to dispose the end portion of the insertion section 2 in a direction in the major axis Ax direction.

On the other hand, a guide groove 51Be for guiding the conductive member 52B into the main body 51Bx w % ben the conductive member 52B is disposed in a predetermined position in the main body 51Bx is formed in each of the other two wall surfaces among the four inner wall surfaces excluding the bottom surface.

In this case, two guide grooves 51Be have a function of guiding both side edge portions 52Bs of the conductive member 52B when the conductive member 52B is disposed in the predetermined position in the main body 51Bx. The two guide grooves 51Be guide the conductive member 52B to a position where a pointed portion 52Bb of the conductive member 52B cuts into the outer layer resin tube 2c (not shown) of the insertion section 2 and further comes into contact with the net-like pipe 2b (not shown). In this case, the guide groove 51Be is set to have an inclination angle of approximately 45 degrees with respect to the major axis Ax of the insertion section 2.

On the other hand, as shown in FIG. 13 and the like, the conductive member 52B in the present embodiment is formed to include a plate-like main body section 52Bc and an arm section 52Be. The plate-like main body section 52Bc includes a slope 52s formed to incline from a connecting section to the arm section 52Be.

A cut-in section 52Bd is formed in a substantially center portion of the plate-like main body section 52Bc. The pointed portion 52Bb is formed in each of opposed two inner sides of the cut-in section 52Bd. In other words, the conductive member 52B includes a plurality of pointed portions 52Bb formed to be opposed in a so-called V shape. Note that the plurality of pointed portions 52Bb may be formed in a U shape.

Axes Y3 and Y4 (see FIG. 13 and FIG. 14) extending along each of the plurality of (in the present embodiment, two) pointed portions 52Bb are formed in parallel to the slope 52s. A surface S3 including the slope 52s as a part thereof is disposed nonparallelly to the major axis Ax. Therefore, the surface S3 is formed to have a predetermined inclination angle with respect to the axis Ax when the conductive member 52B is disposed in a predetermined position in the main body 51Bx of the pipe sleeve 51B.

With such a configuration, the plurality of pointed portions 52Bb are disposed to hold a part of the insertion section 2 inserted into the pipe sleeve 51B and exposed from the opening 51Bb when the conductive member 52B is inserted into the opening 51Bb, which is a cutout, along the guide groove 51Be. At this time, contact sections are formed in a predetermined dimension such that the plurality of pointed portions 52Bb cuts into the outer layer resin tube 2c (not shown) of the insertion section 2 and further comes into contact with the net-like pipe 2b (not shown) to conduct electricity. More specifically, a distance between the contact sections in contact with the net-like pipe 2b among distances among the plurality of pointed portions 52Bb is formed to be smaller than an inner diameter of the outer layer resin tube 2c and equal to or larger than an inner diameter of the net-like pipe 2b.

The arm section 52Be is a part formed to extend from one side edge portion of the plate-like main body section 52Bc. The earth cable 53, which is an earth section, is connected and fixed to the arm section 52Be using soldering or the like. The other components are basically substantially the same as the other components in the respective embodiments explained above.

In the present embodiment configured as explained above, the two pointed portions 52Bb of the conductive member 52B are disposed to hold a part of the insertion section 2 in a state in which the insertion section 2 is inserted through the insertion hole 51Bc of the pipe sleeve 51B and in a state in which the conductive member 52B is guided along the guide groove 51Be and inserted into the main body 51Bx of the pipe sleeve 51B and disposed in a predetermined position. At this time, the two pointed portions 52Bb cut into the outer layer resin tube 2c (not shown) of the insertion section 2 and the contact sections further come into contact with the net-like pipe 2b (not shown) to conduct electricity.

In this state, the adhesive 54 functioning as the fixing member is charged from the opening 51Bb of the main body 51Bx of the pipe sleeve 51B. Consequently, the conductive member 52B is in a state in which the conductive member 52B is fixed to the insertion section 2.

As explained above, according to the fourth embodiment, substantially the same effects as the effects in the respective embodiments explained above can be obtained. Further, according to the present embodiment, the guide groove 51Be for guiding insertion in order to dispose the conductive member 52B in the predetermined position is formed in the main body 51Bx of the pipe sleeve 51B.

Therefore, with this configuration, it is possible to easily and surely perform work for inserting and disposing the conductive member 52B in the main body 51Bx of the pipe sleeve 51B. Since the disposition of the conductive member 52B is surely performed, it is possible to surely bring the pointed portions 52Bb of the conductive member 52B into contact with the net-like pipe 2b of the insertion section 2 in a stable state. Therefore, it is possible to more surely secure electric stability.

Further, in the present embodiment, the plurality of pointed portions 52Bb are provided in the conductive member 52B. The plurality of pointed portions 52Bb are provided to face each other. The plurality of pointed portions 52Bb are disposed to hold the insertion section 2 when the conductive member 52B is disposed in the main body 51Bx of the pipe sleeve 51B. At this time, the plurality of pointed portions 52Bb cut in to hold the outer layer resin tube 2c (not shown) of the insertion section 2 and come into contact with and hold the net-like pipe 2b. Consequently, in the configuration in the present embodiment, the conductive member 52B is in a state in which the conductive member 52B is more strongly fixed to the insertion section 2. Therefore, it is possible to more surely secure electric stability.

Since the plurality of pointed portions 52Bb are disposed to hold the insertion section 2, it is possible to easily and surely secure conductivity of the conductive member 52B and the net-like pipe 2b even with a smaller amount of force.

Note that, in the second to fourth embodiments explained above, an example is only explained in which the adhesive is used as the fixing member for fixing the conductive member to the insertion section. However, the fixing member is not limited to this. As the fixing member, besides the adhesive, other members such as an adhesive tape and a clip member can be applied.

The present invention is not limited to the embodiments explained above. It goes without saying that various modifications and applications can be carried out within a range not departing from the gist of the invention. Further, inventions in various stages are included in the embodiments. Various inventions can be extracted by appropriate combinations in the disclosed plurality of constituent elements. For example, when the problems to be solved by the invention can be solved and the effects of the invention can be obtained even if several constituent elements are deleted from all the constituent elements explained in the one embodiment, a configuration from which the constituent elements are deleted can be extracted as the invention. Further, constituent elements in different embodiments may be combined as appropriate. The present invention is not limited by a specific implementation mode of the invention other than being limited by the appended claims.

What is claimed is:

1. An endoscope comprising: an insertion section comprising a resin layer formed on an outer circumference of a net-like pipe made of metal, the insertion section extending along a longitudinal axis; a conductive member comprising an edge positioned through the resin layer to contact the net-like pipe, and a connector comprising a hole into which the insertion section is inserted and a cutout in which the conductive member is disposed; wherein the edge having a pointed surface configured to cut through the resin layer to contact-the net-like pipe; the cutout further having side edges of the conductive member disposed in one or more guide grooves, respectively, that guide the conductive member to a position where the pointed surface contacts the net-like pipe; the edge comprising a first edge and the pointed surface comprises a first pointed surface; the conductive member includes a second edge having a second pointed surface, the first and second pointed surfaces facing each other, and the first and second pointed surfaces are disposed to hold a part of the insertion section inserted into the connector and exposed to the cutout to each contact the net-like pipe.

2. The endoscope according to claim 1, further comprising a fastener for fixing the conductive member to the insertion section.

3. The endoscope according to claim 2, wherein the fastener is one or more of an adhesive or a screw.

4. The endoscope according to claim 1, further comprising a ground cable having one end connected to the conductive member and another end extending from the conductive member.

5. The endoscope according to claim 1, wherein the cutout is configured to expose a part of a side surface of the insertion section when the insertion section is inserted into the hole.

6. The endoscope according to claim 5, wherein the conductive member is a plate-like member inserted into the cutout.

7. The endoscope according to claim 5, wherein the conductive member has a sloped planar surface terminating in the first and second pointed surfaces, the sloped planar surface is arranged in the cutout non-parallel to the longitudinal axis.

8. The endoscope according to claim 1, wherein the first and second pointed surfaces are formed in on of a V shape or a U shape.

9. An endoscope comprising: an insertion section comprising a resin layer formed on an outer circumference of a net-like pipe made of metal, the insertion section extending along a longitudinal axis; a conductive member comprising an edge positioned through the resin layer to contact the net-like pipe, the edge having a plurality of pointed surfaces configured to cut through the resin layer and to contact the net-like pipe and formed to face each other; a connector comprising a hole into which the insertion section is inserted and a cutout in which the conductive member is disposed; the cutout having side edges of the conductive member disposed in one or more guide grooves, respectively, that guide the conductive member to a position where the pointed surfaces contacts the net-like pipe; wherein the plurality of pointed surfaces are disposed to hold a part of the insertion section inserted into the connector and exposed to the cutout to each contact the net-like pipe.

10. The endoscope according to claim 9, further comprising a fastener for fixing the conductive member to the insertion section.

11. The endoscope according to claim 10, wherein the fastener is an adhesive.

12. The endoscope according to claim 9, further comprising a ground cable having one end connected to the conductive member and another end extending from the conductive member.

13. The endoscope according to claim 9, wherein the cutout is configured to expose a part of a side surface of the insertion section when the insertion section is inserted into the hole.

14. The endoscope according to claim 9, wherein the conductive member is a plate-like member inserted into the cutout.

15. The endoscope according to claim 9, wherein the conductive member having a surface terminating in the plurality of pointed surfaces, the surface is arranged in the cutout non-parallel to the longitudinal axis.

* * * * *